United States Patent
Yang et al.

(10) Patent No.: US 11,925,634 B2
(45) Date of Patent: Mar. 12, 2024

(54) USE OF KOUMINE IN PREPARATION OF MEDICAMENT FOR TREATMENT OF INFLAMMATORY BOWEL DISEASE

(71) Applicant: Fujian Medical University, Fujian Province (CN)

(72) Inventors: Jian Yang, Fujian Province (CN); Changxi Yu, Fujian Province (CN); Ying Xu, Fujian Province (CN); Huihui Huang, Fujian Province (CN)

(73) Assignee: Fujian Medical University, Fuzhou (CN)

( * ) Notice: Subject to any disclaimer, the term of this patent is extended or adjusted under 35 U.S.C. 154(b) by 0 days.

(21) Appl. No.: 17/637,491

(22) PCT Filed: Jul. 10, 2020

(86) PCT No.: PCT/CN2020/101186
§ 371 (c)(1),
(2) Date: Feb. 23, 2022

(87) PCT Pub. No.: WO2021/036537
PCT Pub. Date: Mar. 4, 2021

(65) Prior Publication Data
US 2022/0273640 A1 Sep. 1, 2022

(30) Foreign Application Priority Data

Aug. 23, 2019 (CN) .......................... 201910783284.9

(51) Int. Cl.
*A61K 31/475* (2006.01)
*A61P 1/00* (2006.01)

(52) U.S. Cl.
CPC .............. *A61K 31/475* (2013.01); *A61P 1/00* (2018.01)

(58) Field of Classification Search
CPC .............. A61K 31/475; A61P 1/00; A61P 1/04
USPC ....................................................... 514/410
See application file for complete search history.

(56) References Cited

U.S. PATENT DOCUMENTS

2015/0011767 A1    1/2015  Yu et al.

FOREIGN PATENT DOCUMENTS

| CN | 101322705 A | 12/2008 |
|----|-------------|---------|
| CN | 102293768 A | 12/2011 |
| CN | 103099776   | * 5/2013 |
| CN | 104147008 A | 11/2014 |
| CN | 109893528 A | 6/2019 |
| CN | 109953991 A | 7/2019 |

OTHER PUBLICATIONS

International Search Report for PCT/CN2020/101186, dated Oct. 12, 2020, 3 pages.

(Continued)

*Primary Examiner* — Taylor V Oh
(74) *Attorney, Agent, or Firm* — Blank Rome LLP

(57) ABSTRACT

The present invention relates to novel use of koumine, an alkaloid monomer from *Gelsemium elegans* Benth., or a pharmaceutically acceptable salt thereof, and more particularly to use of koumine or its pharmaceutically acceptable salt in the preparation of a medicament for the treatment of inflammatory bowel disease.

17 Claims, 6 Drawing Sheets

(56) References Cited

OTHER PUBLICATIONS

Zhi-hang Yuan, et al., "Effect of Koumine on the Inflammation of RAW264.7 Cells Induced by LPS", Chin J Vet Sci, Aug. 2017, vol. 37, No. 8, pp. 1553-1557.
Qi-lin Tang et al., "Research Progress of Tumor Necrosis Factor Alpha and Interleukin-6 in the Pathogenesis of Inflammatory Bowel Disease", Medical Recapitulate, Apr. 2014, vol. 20, No. 7, pp. 1174-1176.
I. Peter, et al., "Anti-Tumor Necrosis Factor Therapy and Incidence of Parkinson Disease Among Patients with Inflammatory Bowel Disease", JAMA Neurol., https://pubmed.ncbi.nlm.nih.gov/29710331; Aug. 1, 2018, 2 pgs.
Decision of Rejection of Chinese Patent Application No. 2019107832849 along with English language translation dated Aug. 26, 2023, 8 pages.

* cited by examiner

USE OF KOUMINE IN PREPARATION OF MEDICAMENT FOR TREATMENT OF INFLAMMATORY BOWEL DISEASE

RELATED APPLICATIONS

The present application is a national phase application of PCT/CN2020/101186, filed Jul. 10, 2020, which claims priority from Chinese Patent Application No. 201910783284.9, Aug. 23, 2019. The entire contents of which are hereby incorporated by reference.

FIELD OF THE INVENTION

The present invention relates to novel use of koumine, an alkaloid monomer from *Gelsemium elegans* Benth., or a pharmaceutically acceptable salt thereof, and more particularly to use of koumine or its pharmaceutically acceptable salt in the preparation of a medicament for the treatment of inflammatory bowel disease.

DESCRIPTION OF THE PRIOR ART

In a broad sense, inflammatory bowel disease (IBD) is a general term for a variety of diseases that feature intestinal inflammation as the principal manifestation, such as infectious bowel inflammation and non-infectious inflammatory bowel diseases (including toxic bowel inflammation, ischemic bowel disease, radiation bowel inflammation, autoimmune bowel inflammation, chronic nonspecific bowel inflammation, etc.). IBD in a narrow sense includes ulcerative colitis (UC) and Crohn's disease (CD). IBD is characterized mainly by intestinal inflammation and epithelial destruction, and its primary symptoms include prolonged diarrhea, with or without profuse bleeding, abdominal pain, weight loss, fever, etc. At a late stage of this disease, an elevated systemic level of inflammatory factors may lead to involvement of multiple systems and multiple organs and an increased chance of developing colorectal cancer, which severely threaten human health and life.

At present, anti-IBD treatment is relying mostly on medication. Conventional medicaments for this purpose include steroids and immunosuppressive drugs such as, among others, methotrexate, azathioprine and 6-mercaptopurine. Although such medication is low in cost, it is time-consuming and slow in healing, tending to lead to a waste of the precious treatment time. As biological agents, TNF-α inhibitors (e.g., infliximab, adalimumab) are being considered as the most effective medicaments currently available for the treatment of IBD. However, these biological agents are generally expensive, easy to degrade, poorly orally absorbable and associated with the risks of causing tuberculosis and significantly increasing the likelihood of the development of serious infections and tumors. These shortcomings greatly limit their application. Thus, there still exists a high need for safe and effective novel medicaments for anti-IBD treatment.

Discovering monomers with anti-IBD activity in medicinal plants and conducting in-depth exploratory research on critical scientific and technological issues regarding them provide an important way to develop new therapeutic medicaments.

Koumine, an indole alkaloid found in *Gelsemium elegans* Benth., is the richest monomer in the total alkaloids of *Gelsemium elegans* Benth. and shows relatively low toxicity. Chinese Patent Application Publication No. CN 101323618 B discloses a method for extracting and separating koumine from *Gelsemium elegans* Benth. plants. The inventors of this application have discovered, during a pharmacodynamic study of koumine, its novel use for anti-IBD treatment.

SUMMARY OF THE INVENTION

In one aspect of the present invention, there is provided use of koumine or a pharmaceutically acceptable salt thereof in the preparation of a medicament for the treatment of inflammatory bowel disease in a subject in need.

In another aspect of the present invention, there is provided koumine or a pharmaceutically acceptable salt thereof for the treatment of inflammatory bowel disease in a subject in need.

In a further aspect of the present invention, there is provided a method for the treatment of inflammatory bowel disease in a subject in need thereof, the method comprising administering a therapeutically effective amount of koumine or a pharmaceutically acceptable salt thereof or a therapeutically effective amount of a medicament comprising koumine or a pharmaceutically acceptable salt thereof to the subject.

BRIEF DESCRIPTION OF THE DRAWINGS

FIG. 1-A shows body weight variation (%) of the mice in different groups from D0 to D7. The histogram in FIG. 1-B shows body weight variation (%) of the mice in the individual groups on D7. Results are presented as means±standard errors of the means (SEM), and *$p<0.05$, $p<0.01$, *$p<0.001$, as compared to a model group.

In FIG. 2-B, results are presented as means±standard errors of the means (SEM), and *$p<0.05$, ***$p<0.001$, as compared to a model group.

In FIG. 7-B, results are presented as means±standard errors of the means (SEM), and $p<0.01$, *$p<0.001$, as compared to a model group.

In FIG. 10, results are presented as means±standard errors of the means (SEM), p<0.05 as compared to a vehicle control group, and p<0.01, *p<0.001 as compared to a model group.

DETAILED DESCRIPTION OF THE PREFERRED EMBODIMENTS

Figure 1:
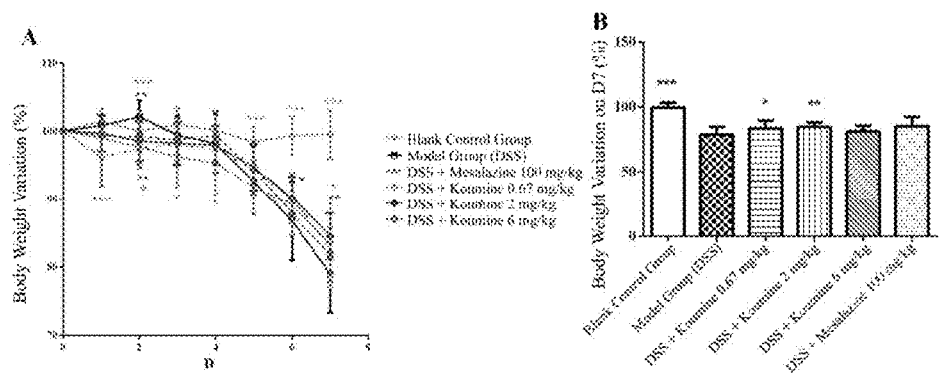
FIG. 1 shows an effect of koumine on body weight variation (%) of mice with DSS-induced bowel inflammation.

The present invention will now be described in detail with reference to representative embodiments thereof. These embodiments are merely exemplary and should not be construed to limit the scope of the invention in any way. Rather, the invention is intended to cover all alternatives, modifications and equivalents within the scope of the invention as defined by the claims.

Unless otherwise indicated, all technical and scientific terms used herein have the same meaning as commonly understood by one having ordinary skill in the art to which the invention pertains.

As used herein, the term "koumine" refers to an alkaloid monomer obtained from *Gelsemium elegans* Benth. or by synthesis, which has the following structural formula and the molecular formula $C_{20}H_{22}N_2O$:

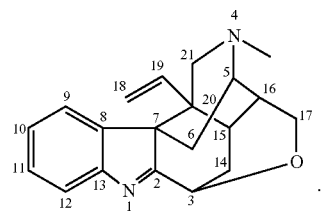

As used herein, a pharmaceutically acceptable salt of koumine includes a salt formed from koumine and an organic or inorganic acid. Exemplary pharmaceutically acceptable salts include, but are not limited to, hydrochloride, sulphate, hydrobromide, hydroiodide, nitrate, bisulphate, phosphate, acid phosphate, citrate, acetate, oxalate, isonicotinate, lactate, salicylate, acid citrate, tartrate, oleate, tannate, pantothenate, bitartrate, ascorbate, succinate, maleate, gentisate, fumarate, gluconate, glucuronate, formate, benzoate, glutamate, mesylate, ethanesulfonate, benzenesulfonate, tosylate and pamoate. Preferably, the pharmaceutically acceptable salt is koumine hydrochloride.

As used herein, the term "pharmaceutically acceptable" means that a compound, composition or carrier is suitable to be administered to a subject for the purpose of the use or method described herein without undesirable harmful side effects.

As used herein, the term "subject" refers to mammals including, but not limited to, primates (e.g., humans, monkeys, chimpanzees, gorillas, etc.), rodents (e.g., rats, mice, gerbils, hamsters, ferrets and other analogous rodents), lagomorphs, porcines (e.g., pigs, piglets), equines, canines, felines, etc. In preferred embodiments, the subject is a mammal, preferably a human.

As used herein, the term "treatment" refers to complete or partial healing or elimination of a disease, disorder, or pathological condition, including but not limited to, one or a combination of two or more selected from: alleviating or eliminating the cause of the disease, disorder or pathological condition; ameliorating or eliminating a pathological change thereof; alleviating or eliminating one or more symptoms thereof slowing or stopping its progression; lessening its severity; lowering its rate of incidence; reducing its recurrence; and improving its prognosis.

The inventors of this application have found from experiments that koumine or a pharmaceutically acceptable salt thereof (e.g., hydrochloride) exhibits significant therapeutic effects on IBD and is able to relieve weight loss, loose stools, bloody stools and other IBD symptoms, ameliorate inflammation, hemorrhage and other pathological manifestations of affected colonic tissue and suppress the expression of myeloperoxidase (MPO) in inflammatory colonic tissue.

Accordingly, in one aspect, the present invention provides use of koumine or a pharmaceutically acceptable salt thereof in the preparation of a medicament for the treatment of inflammatory bowel disease in a subject in need thereof.

In another aspect, the present invention provides koumine or a pharmaceutically acceptable salt thereof for the treatment of inflammatory bowel disease in a subject in need thereof.

In a further aspect, the present invention provides a method for the treatment of inflammatory bowel disease in a subject in need thereof, the method comprising administering a therapeutically effective amount of koumine or a pharmaceutically acceptable salt thereof or a therapeutically effective amount of a medicament comprising koumine or a pharmaceutically acceptable salt thereof to the subject.

In some embodiments, koumine or the pharmaceutically acceptable salt thereof ameliorates or eliminates a pathological change of inflammatory bowel disease, including inflammatory cell infiltration, hyperemia, hemorrhage, edema, mucosal erosions and ulcers, glandular atrophy, branching or distorted irregularities, reduced goblet cells and mucus therein, pseudopolyps, dysplasia or the like. In some other embodiments, it alleviates or eliminates one or more symptoms of inflammatory bowel disease such as, but not limited to, diarrhea, hematochezia, abdominal pain, weight loss and fever, with diarrhea, hematochezia and/or weight loss being preferred. In some other embodiments, it slows or stops progression of inflammatory bowel disease. In some other embodiments, it lessens the severity of inflammatory bowel disease. In some other embodiments, it reduces recurrence of inflammatory bowel disease. Additionally or alternatively, in some other embodiments, it improves the prognosis of inflammatory bowel disease.

In some embodiments, the inflammatory bowel disease is selected from: infectious bowel inflammation; non-infectious inflammatory bowel diseases including toxic bowel inflammation, ischemic bowel disease, radiation bowel inflammation, autoimmune bowel inflammation and chronic nonspecific bowel inflammation; and any combination thereof. As used herein, the term "chronic nonspecific bowel inflammation" includes ulcerative colitis, Crohn's disease, etc. In some embodiments, the inflammatory bowel disease is ulcerative colitis or Crohn's disease. In some embodiments, the inflammatory bowel disease is ulcerative colitis. In some embodiments, the inflammatory bowel disease is Crohn's disease.

In some embodiments, the medicament comprises koumine or the pharmaceutically acceptable salt thereof as a sole active ingredient.

In some embodiments, the medicament further comprises one or more other active ingredients. In such embodiments, koumine or the pharmaceutically acceptable salt thereof and the one or more other active ingredients may be separately formulated so that they are contained in multiple individual compositions, or together formulated in a single composition that contains them.

In some embodiments of the method of the present invention, koumine or the pharmaceutically acceptable salt thereof is administered to the subject as a sole active ingredient, or in combination with the one or more other active ingredients. In the case of the combined administration, koumine or the pharmaceutically acceptable salt thereof and the one or more other active ingredients may be administered to the subject either simultaneously or sequentially. The combined administration includes administering individual compositions separately containing koumine or the pharmaceutically acceptable salt thereof and the one or more other active ingredients simultaneously or sequentially in any order, or administering a single composition containing both koumine or the pharmaceutically acceptable salt thereof and the one or more other active ingredients.

The one or more other active ingredients are one or more chemotherapeutic or biotherapeutic agents, or a combination thereof, which are known in the art to have therapeutic effects on inflammatory bowel disease.

The medicament optionally comprises one or more pharmaceutically acceptable carriers such as excipients, disintegrants, diluents, binders, glidants, lubricants, pH adjusters, preservatives, dispersants, suspension aids, ointment bases, emulsifiers, emollients, penetration enhancers, surfactants, propellants, flavoring agents, sweeteners, drug release modifiers, etc. Those skilled in the art may select suitable carrier(s) according to the medicament's desired dosage form, mode of administration, release characteristics, etc.

The terms "including", "comprising", "having", "containing" or "involving", as well as other variations thereof used herein, are inclusive or open-ended terms that do not exclude other unlisted elements or method steps, even if the other such elements or method steps are not necessarily present (i.e., these terms also encompass the terms "consisting essentially of" and "consisting of").

The medicament may be formulated in solid, semi-solid or liquid dosage forms suitable to be administered in any well-recognized mode of administration available in the art, including but not limited to: (1) those suitable for oral administration, such as tablets, capsules, powders, granules, lozenges, aqueous or non-aqueous solutions or suspensions, syrups, etc.; (2) those suitable for parenteral administration, such as subcutaneous, intramuscular or intravenous injections such as sterile solutions or suspensions; (3) those suitable for topical administration such as plasters, ointments, creams, sprays, gels or the like for application to skin or mucous membranes; (4) those suitable for transdermal administration, such as patches, gel plasters, etc.; (5) those suitable for vaginal administration, enema administration (colonic perfusion using a delivery device inserted from the anus to the colon through the rectum), rectal administration, such as suppositories, enemas, emulsions, gels, effervescent tablets or the like.

As used herein, the term "therapeutically effective amount" refers to an amount allowing the active ingredient(s), when administered, to achieve the desired therapeutic effect of said use or method.

In the use or method described herein, dosage of koumine or the pharmaceutically acceptable salt thereof and/or the one or more other active ingredients generally depends on a variety of factors, including the subject under treatment, the severity of the disease or condition, the rate of administration and the judgment of the prescribing physician. In general, an effective dose is about 0.0001 to about 50 mg per kg of body weight per day, e.g., about 0.0005 to about 25 mg/kg/day, or about 0.001 to about 5 mg/kg/day (administered in a single dose or divided doses). For a 70 kg human, this will amount to a total of about 0.007 mg/day to about 3500 mg/day, e.g., about 0.035 mg/day to about 1750 mg/day, or about 0.07 mg/day to about 350 mg/day. In some instances, dosage levels below the lower limit of the aforesaid range can be adequate, while in other cases still larger doses can be employed without causing any harmful side effect, and if necessary, such larger doses can be divided into several small doses for administration throughout the day.

Koumine or the pharmaceutically acceptable salt thereof and/or the one or more other active ingredients may be present in the medicament, or used in the method, at an amount of about 0.001 mg to about 500 mg, for example, about 0.01-200 mg, about 0.1-20 mg or about 0.5-10 mg, with about 0.1-20 mg being preferred.

The present invention will be described in greater detail below with reference to examples, which, however, do not limit the invention in any sense. The scope of the present invention is only defined by the claims.

EXAMPLES

Example 1. Therapeutic Effects of Koumine on DSS-Induced Bowel Inflammation in Mice Dextran sulfate sodium (DSS) has an anticoagulant effect and, when orally administered to experimental animals, can cause hyperemia, ulcers, submucosal edema in bowel tissue and other pathological manifestations closely similar to those of clinical IBD patients. Models of DSS-induced bowel inflammation can be taken as basic models for studying the pathogenesis of UC and even IBD and evaluating the efficacy of therapeutic medicaments. In this example, therapeutic effects of koumine were evaluated in a C57BL/6 mouse model of DSS-induced bowel inflammation with the animals' body weight, defecation, pathological manifestations of colonic tissue, expression of MPO in colonic tissue and the like as indicators.

1. Materials 1.1. Experimental Animals Six to eight week old healthy male SPF C57BL/6 mice (weighing 18-22 g) were purchased from Shanghai SLAC Laboratory Animal Co., Ltd. (License No. SOCK (Shanghai) 2017-0005). Prior to study start, the mice were acclimated for 7 days until their body weights reached 20±2 g. They were bred under conditions of a 12/12-h light-dark cycle (light on 8:00-20:00), constant temperature (20-26° C.) and constant humidity (40-70%), with food and water provided ad libitum. Experimental operations were conducted in accordance with regulations of international and local committees on care and use of laboratory animals (the same applies below).

1.2. Medicaments and Reagents Koumine hydrochloride ($C_{20}H_{22}N_2O \cdot HCl$) (in the form of a powder) was prepared in the School of Pharmacy, Fujian Medical University (Batch No. KM201610, with a purity of 99.99% as determined by high performance liquid chromatography), stored at 4° C. in the dark, and dissolved in normal saline to a desired concentration before use. DSS was purchased from MP Biomedicals, USA and fully dissolved in distilled water to a desired concentration before use. Mesalazine enteric coated tablets were purchased from Heilongjiang Tianhong Pharmaceutical Co., Ltd. A citrate (pH=6.0) antigen retrieval solution, BSA, an anti-myeloperoxidase primary antibody, an HRP-conjugated goat anti-rabbit secondary antibody and a histochemistry kit for DAB staining were purchased from Wuhan Servicebio Technology Co., Ltd. (the same applies below).

1.3. Experimental Instruments

A Centrifuge 5430 R refrigerated high speed centrifuge from eppendorf, Germany; an Epoch microplate reader from BioTek, USA; a FINESS ME microtome, an EXCELSIOR ES hydroextractor and a HISOTAR embedding unit from Thermo Scientific, USA; and a veterinary anesthesia vaporizer from MIDMARK, USA (the same applies below).

2. Methods

Fifty-one healthy SPF C57BL/6 mice were randomly assigned into a blank control group (n=6), a model group (n=9) and 4 treatment groups (n=9 for each) respectively administered with low (0.67 mg/kg), medium (2 mg/kg) and high (6 mg/kg) doses of koumine, as well as mesalazine (100 mg/kg) as a positive control. A mouse model of DSS-induced bowel inflammation was established by allowing the mice in the model group and the individual treatment groups to have free access to a 2.5% DSS solution in water for 8 days and providing ad libitum access to normal water to the mice in the blank control group. From the day of induction (D0), the mice in the treatment groups received intragastric administration (0.1 mL/10 g) once a day for 9 consecutive days (D0-D8), while those in the control and model groups were given the same volumes of normal saline also by intragastric administration throughout the same period. Body weight measurements were taken and fecal occult blood tests were performed daily. One hour after the last administration (D8), the mice were sacrificed by cervical dislocation under anesthesia. Immediately after that, a bowel segment from the terminal ileum to the anus was removed from each mouse, and a length from the ileocolonic junction to the anus was measured and recorded. Colonic tissue was taken 1 cm away from the anus for histopathological examination, as well as for immunohistochemical detection for the expression of MPO. Additionally, colonic tissue was taken 1-2 cm away from the anus for MPO activity determination.

3. Results 3.1. Effect of Koumine on Defecation and Body Weights of Mice with DSS-Induced Bowel inflammation After the mice in the model group began to take the DSS solution, progressive changes in fecal characteristics and hemorrhage occurred gradually. At the beginning (D1-D2), more times of defecation and increasingly softer droppings tested, however, negative for occult blood were observed, followed by prevalence of loose feces and subsequent liquid feces sticking to the anus. From D3, there began to be positive fecal occult blood tests followed by gradual shifting to visible blood in loose feces, sticky scab-like bloody feces around the anus or fresh blood in feces, decreased appetite and weight loss. As shown in FIG. 1, koumine could alleviate the symptom of weight loss in mice with bowel inflammation. An average body weight of the mice in the low-dose group (0.67 mg/kg) was significantly higher than that of those in the model group as early as on the seventh day of administration (D6) ($p<0.05$), and an average body weight of the mice in the medium-dose group (2 mg/kg) became significantly higher than that of those in the model group as early as from the sixth day of administration (D5) ($p<0.05$ and $p<0.01$). The mice in the groups treated with the medium and high doses of koumine all had fewer times of defecation and mitigated hematochezia, indicating that koumine improved the symptoms of bowel inflammation in the model mice.

Figure 2:
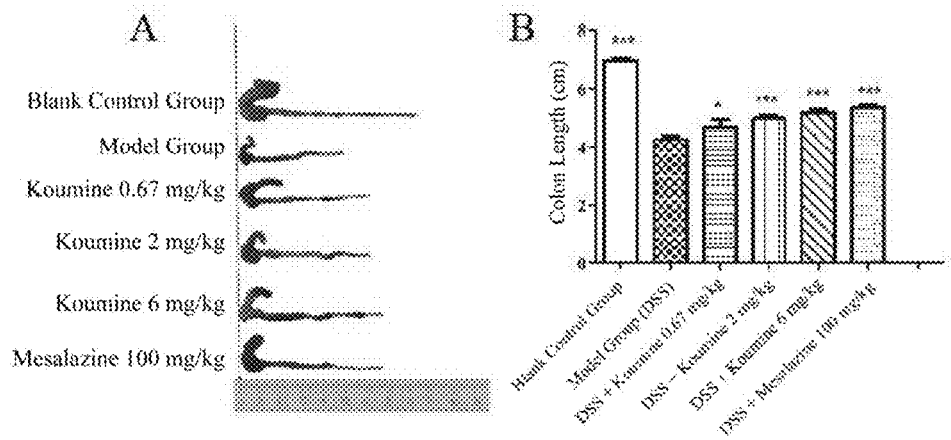
FIG. 2 shows an effect of koumine on colon length of mice with DSS-induced bowel inflammation.

3.2. Amelioration of Morphological Manifestations of Colonic Tissue of Mice with DSS-Induced Bowel Inflammation by Koumine Observations of colonic tissue harvested from the sacrificed mice revealed a reddish or translucent colon color, easy separability of bowel tissue, absence of adhesions, intact bowel mucosa visible after the intestinal lumen was opened and no obvious hyperemia or edema in the blank control group, as well as a considerably and significantly shorter colon length compared to the blank control group mice ($p<0.001$; FIG. 2), presence of obvious adhesions, increased brittleness of bowel tissue leading to easy breakage, hyperemia of bowel mucosa and a thickened bowel wall in the model group. Administering koumine could ameliorate damage, hyperemia and the like caused by the irritating DSS to the bowel mucosa and dose-dependently reduce colon shortening of the mice with bowel inflammation. The low-dose group mice had a colon length significantly greater than that of the model group on the eighth day of administration ($p<0.05$; FIG. 2).

Figure 3:
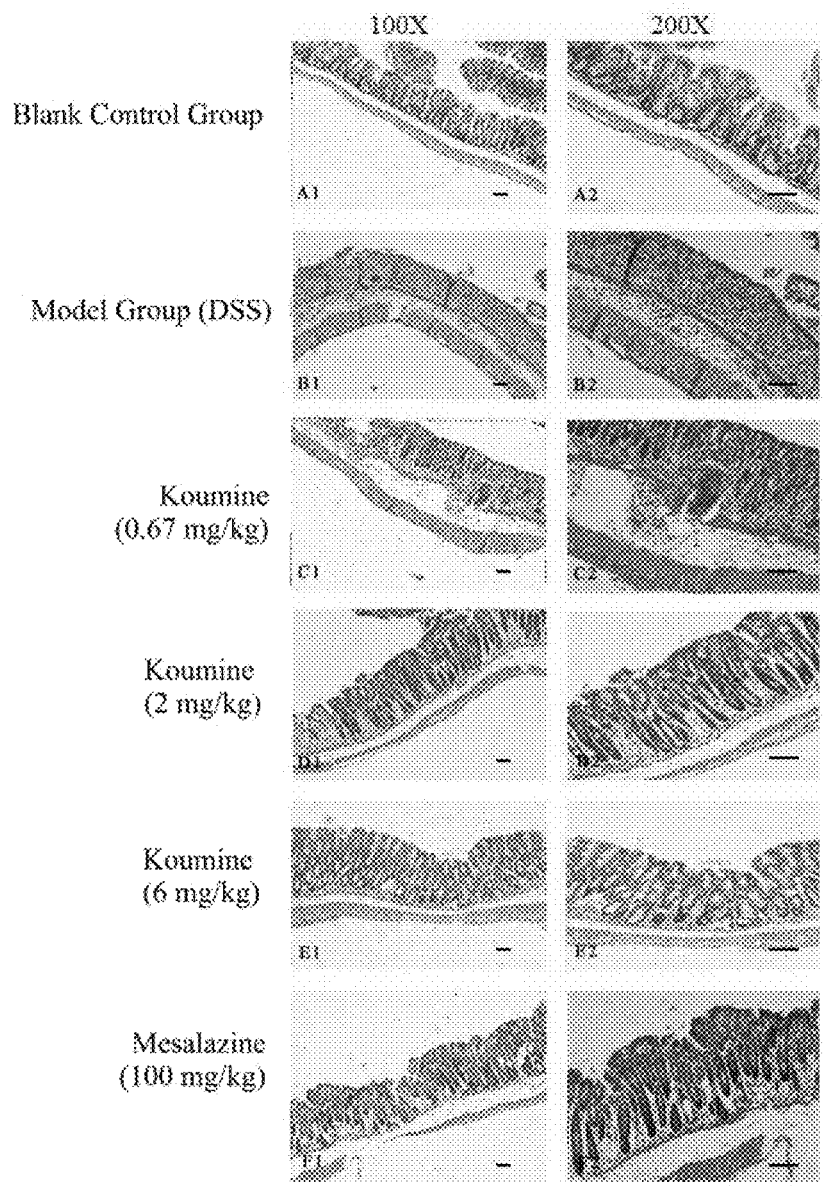
FIGS. 3 to 4 show effects of koumine on microscopic manifestations of HE-stained colonic tissue of mice with DSS-induced bowel inflammation (FIG. 3) and on microscopic histopathological scoring thereof (FIG. 4). Results of histopathological scoring are presented as means±standard errors of the means (SEM), ###$p<0.001$ as compared to a blank control group, and **$p<0.01$ as compared to a model group.
Figure 4:
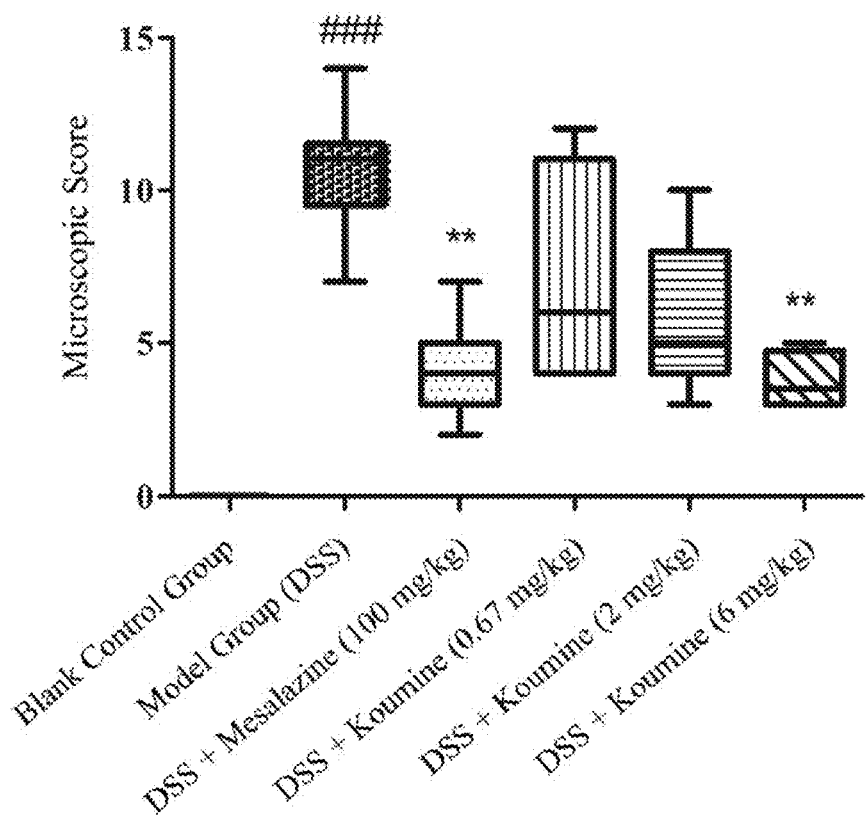

HE staining showed structural intactness of the individual colonic layers, presence of colonic crypts, abundant mucus in goblet cells and absence of ulcers and noticeable inflammatory cell infiltration in the colons of the blank control group mice (FIG. 3: A1-A2). Atrophy or even loss of colonic crypts, irregularly arranged glands, infiltration of a large number of inflammatory cells and hemorrhage in the mucosa and obvious edema of the muscularis mucosae were microscopically observed in colonic tissue of the model group mice (FIG. 3: B1-B2). In colonic tissue of the mice given koumine, reduced inflammatory cell infiltration, completeness of the colonic structure increasing with the dose of koumine, relatively regularly arranged glands in the lamina propria, more goblet cells, milder submucosal edema and absence of noticeable ulcers were seen (FIG. 3: C1-C2, D1-D2 and E1-E2). Presence of goblet cells, intact epithelium and relatively regularly arranged glands were observed in colonic tissue of the mice in the group treated with the positive control mesalazine (FIG. 3: F1-F2), and obvious improvements over the model group mice were also confirmed microscopically. Histopathological scoring indicated that koumine and mesalazine at their high doses were both able to significantly inhibit increases in the sore of the model group ($p<0.01$; FIG. 4).

Figure 5:
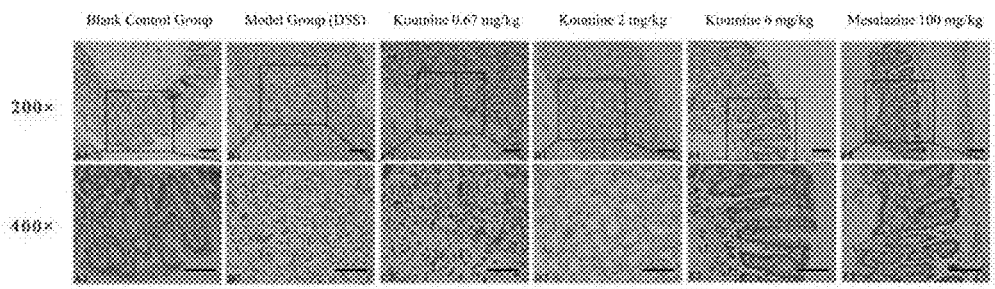
FIG. 5 shows microscopic images of immunohistochemically stained murine colonic tissue, showing an effect of koumine on the expression of myeloperoxidase (MPO) in colonic tissue of mice with DSS-induced bowel inflammation.

3.3. Inhibitory Effect of Koumine on Expression of MPO in Colonic Tissue of Mice with DSS-Induced Bowel Inflammation Immunohistochemical results demonstrated regularly arranged glands with sparse expression of brownish yellow granular MPO in colonic tissue of the blank control group mice (FIG. 5: A1-A2), and considerably increased expression of MPO and dense infiltration into the lamina propria in the model group mice (FIG. 5: B1-B2). Koumine administered at the low dose did not lead to any noticeable decrease in the expression of MPO (FIG. 5: C1-C2), while both koumine at the medium and high doses and mesalazine lowered the expression of MPO to different extents (FIG. 5: D1-D2, E1-E2 and F1-F2).

Examples 2. Therapeutic Effects of Koumine on OXA-Induced Colitis in Mice

Oxazolone (OXA) is a hapten that has been shown to induce contact hypersensitivity reactions in animals and can also be used to induce colitis in mice. OXA-induced colitis causes lesions primarily in the distal colon and resembles human IBD in terms of histological characteristics and distribution of inflammation, which can be manifested as a decrease in goblet cells.

1. Materials 1.1. Experimental Animals

Six to eight week old healthy male SPF BALB/c mice were purchased from Shanghai SLAC Laboratory Animal Co., Ltd. (License No. SOCK (Shanghai) 2017-0005).

1.2. Medicaments and Reagents

The same koumine hydrochloride and mesalazine as in Example 1 were used. OXA was purchased from Sigma, USA and prepared in the form of a solution before use by fully dissolving it in absolute ethanol preheated to 35° C. When used for an enema, the solution was diluted 1-fold with normal saline to a desired concentration. Absolute ethanol was purchased from Merck, Germany. All the other reagents were the same as in Example 1.

1.3. Experimental Instruments

The same instruments were used as in Example 1.

2. Methods

Seventy-four BALB/c mice were randomly assigned into a blank control group (n=6), a vehicle control group (n=10), a model group (n=19) and low-dose (n=10), medium-dose (n=9) and high-dose (n=12) koumine treatment groups and another treatment group (n=8) administered with mesalazine as a positive control. A mouse model of OXA-induced UC was established by sensitizing and then giving enemas to the mice in the model group and the individual treatment groups. Specifically, each of the mice was anesthetized and sensitized by drop-wise applying a 3% solution (150 μL) of OXA in absolute ethanol to a shaved abdominal area (about 1.5 cm×1.5 cm), and received an enema using a 1% solution of OXA in 50% ethanol (100 μL) five days following the sensitization (D0). The mice in the vehicle and blank control groups were treated similarly, except for drop-wise application of 150 μL absolute ethanol and normal saline in the sensitization phase, respectively, and use of 100 μL of 50% ethanol and the same volume of normal saline in the enema phase, respectively. From the day of enema administration (D0), the mice in the treatment groups received intragastric administration (0.1 mL/10 g) once a day for 4 consecutive days (D0-D3). The daily dosage of koumine and the positive control mesalazine to the treatment groups was the same as in Example 1, and the vehicle control group was given the same volumes of 50% ethanol. Bowel inflammation evaluation of the animals was conducted in the same manner using the same indicators as in Example 1.

3. Results

Figure 6:
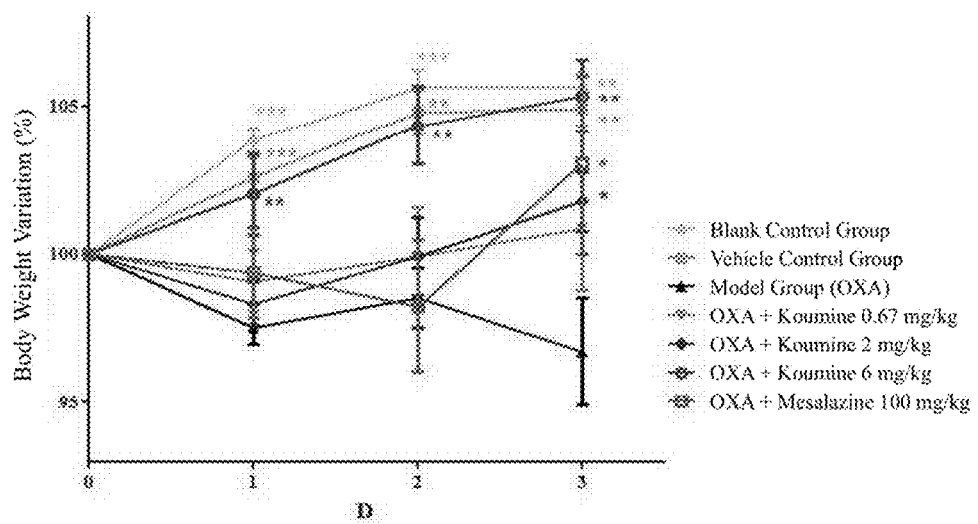
FIG. 6 shows an effect of koumine on body weights (%) of mice with OXA-induced colitis. Results are presented as means±standard errors of the means (SEM), and *$p<0.05$, $p<0.01$, *$p<0.001$, as compared to a model group.

3.1. Effect of Koumine on Defecation and Body Weights of Mice with OXA-Induced Colitis Twenty-four hours after the enemas were given, the mice in the model group developed anorexia, laziness and soft or even loss feces. These symptoms aggravated on the second day after the enemas were administered and then remained the same. No visible blood in feces was observed, and the fecal occult blood tests were weakly positive. A decreasing trend of body weight was identified. Although the mice in the vehicle control group exhibited slight increases in the number of defecation and softness of the produced feces 24 h after the enemas were given, both the defecation count and fecal characteristics became normal 3 days after the administration of the enemas. As shown in FIG. 6, koumine can alleviate body weight loss of mice with colitis in a dose-dependent manner. The positive control mesalazine (100 mg/kg) appeared to have an effect of alleviating body weight loss comparable to that of the medium dose of koumine (2 mg/kg). The percentage of the animals' body weight in the value on D0 became significantly higher than that of the model group as late as on the fourth day (D3) (p<0.05).

Figure 7:
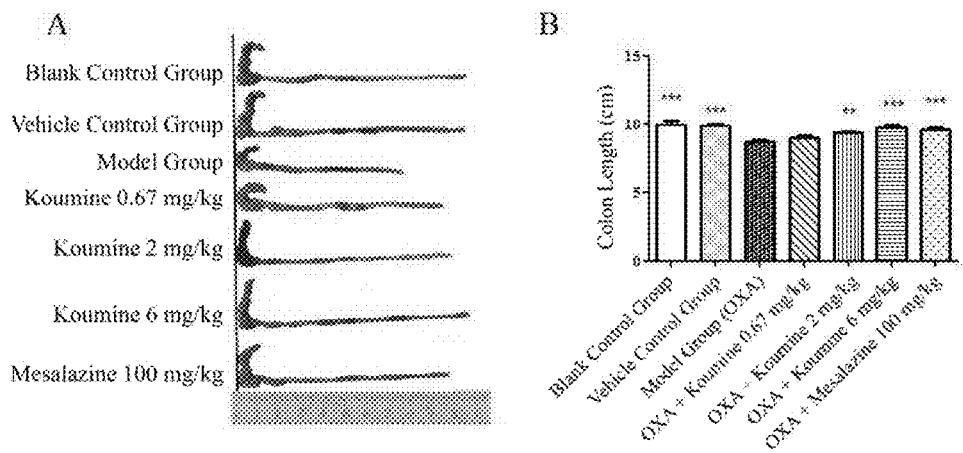
FIG. 7 shows an effect of koumine on colon length of mice with OXA-induced colitis.

3.2. Amelioration of Histomorphological Manifestations of Colonic Tissue of Mice with Colitis by Koumine The mice were sacrificed by cervical dislocation under anesthesia 4 days following the administration, and their abdominal cavities were opened. A reddish or translucent colon color, intact bowel mucosa and absence of obvious hyperemia or edema were observed in the mice of the blank and vehicle control groups, and typical manifestations of colitis including obvious local redness and swelling, hyperemia and colonic wall thickening, as well as a considerably shortened colon length with a significant difference from that of the vehicle control group, in the model group mice (p<0.001; FIG. 7). The low dose of koumine (0.67 mg/kg) appeared to not mitigate the manifestations including colon hyperemia, redness and swelling in the mice with colitis in a noticeable fashion, but it could significantly reduce their colon shortening (p<0.01). The mice in the treatment group administered with the medium dose of koumine (2 mg/kg) were not seen with severe redness and swelling, hyperemia or other inflammatory manifestations in their colonic tissue, and remarkable relief of most manifestations of colonic tissue of the mice in the treatment group given the koumine at the high dose (6 mg/kg) was confirmed. Koumine's positive effect on colon length of the mice with colitis was dose-dependent, and the effect of the positive control mesalazine was comparable to that of koumine at 6 mg/kg.

Figure 8:
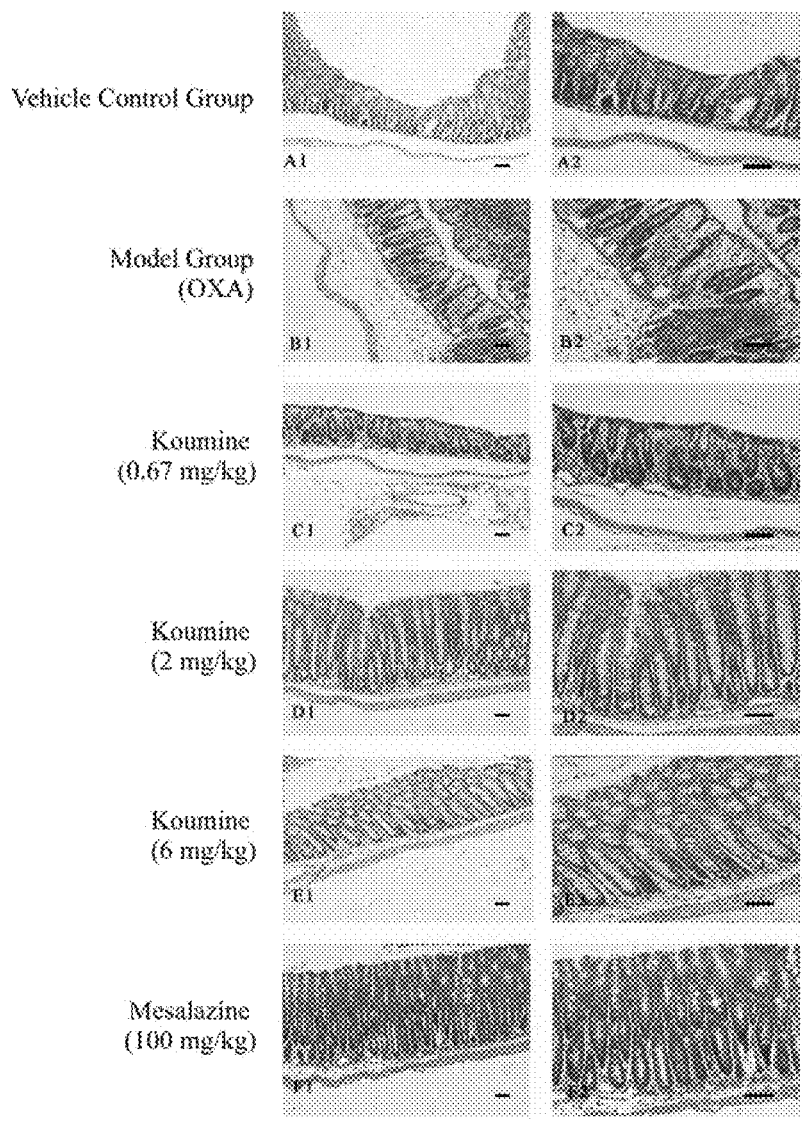
FIG. 8 shows an effect of koumine on microscopic manifestations of HE-stained colonic tissue of mice with OXA-induced colitis.

HE staining showed regularly arranged glands with intact structures and absence of ulcers and obvious inflammatory cell infiltration in the colons of the vehicle control group mice (FIG. 8: A1-A2), obvious ulcers, hemorrhage, structurally damaged crypts and massive infiltration of inflammatory cells dominated by neutrophils etc. in colonic tissue of the model group mice (FIG. 8: B1-B2), slightly milder symptoms than the symptoms of the model group still with histological structural incompleteness and massive infiltration of inflammatory cells in the low-dose koumine treatment group (0.67 mg/kg) (FIG. 8: C1-C2), and infiltration of only a small number of inflammatory cells in both the medium- and high-dose koumine (2 mg/kg and 6 mg/kg) and mesalazine treatment groups (FIG. 8: D1-D2, E1-E2 and F1-F2) compared to the other groups.

Figure 9:
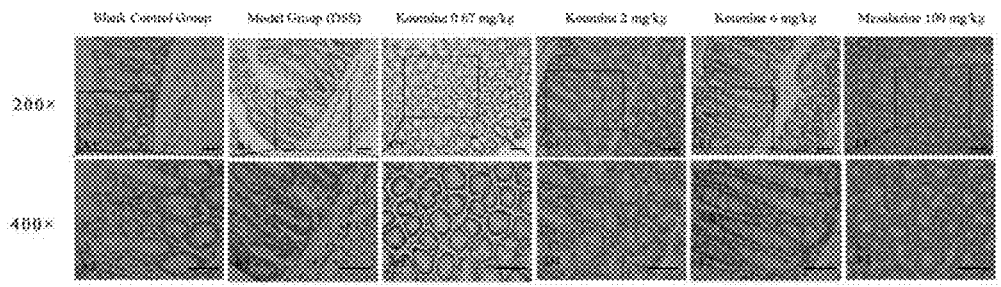
FIGS. 9 to 10 show effects of koumine on expression (FIG. 9) and enzymatic activity (FIG. 10) of MPO in colonic tissue of mice with OXA-induced colitis.
Figure 10:
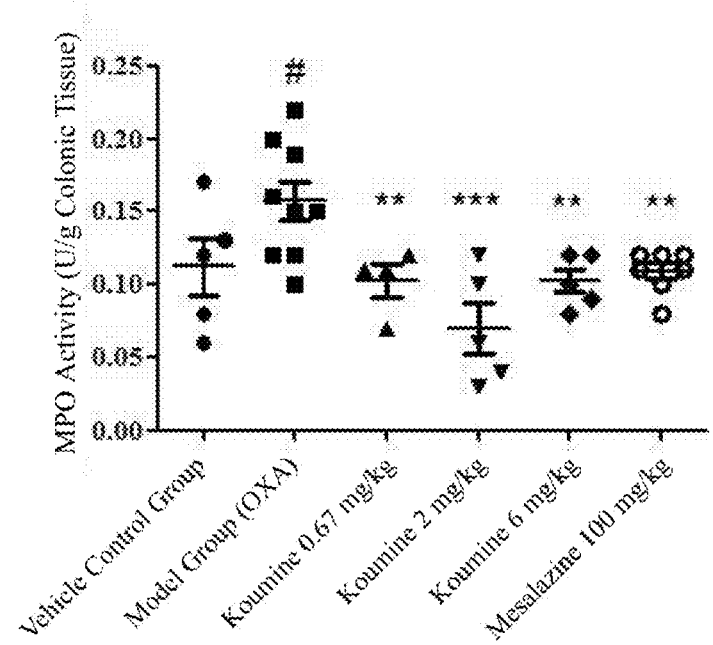

3.3. Inhibitory Effect of Koumine on Expression and Activity of MPO in Colonic Tissue of Mice with Colitis Immunohistochemical results showed intact glands without noticeable expression of brownish yellow granular MPO in colonic tissue of the vehicle control group mice (FIG. 9: A1-A2), considerably increased expression of MPO which infiltrated into deeper layers, in particular, densely in the submucosa in the model group (FIG. 9: B1-B2), and suppressed expression of MPO to varying extents in the groups administered with koumine at the different doses and mesalazine (FIG. 9: C1-C2, D1-D2, E1-E2 and F1-F2). It was found in associated activity assays of MPO in colonic tissue homogenates (FIG. 10) that an average enzymatic activity of MPO in colonic tissue of the model group mice was significantly higher than that of the vehicle control group (p<0.05), and that the administration of koumine at the different doses and mesalazine inhibited OXA-induced increases in MPO activity and significantly reduced enzymatic activity per unit weight (p<0.01, p<0.001). These results suggested that koumine had a certain inhibitory effect on both the quantity and activity of MPO in colonic tissue of OXA-induced mice.

In summary, although the effects of koumine slightly varied between the different IBD models, it alleviated weight loss, loose feces, bloody feces and other symptoms of bowel inflammation in the model mice and improved pathological manifestations and enzymatic changes of their inflammatory colonic tissue, indicating that koumine is effective in treating inflammatory bowel disease.

All publications and patent applications cited in this application are indicative of the state of the art to which this disclosure pertains. They are all incorporated herein by reference in their entirety.

From the foregoing description, one skilled in the art can ascertain the essential features of this invention and, without departing from the spirit and scope thereof, can make various changes and modifications of the invention to adapt it to various uses and conditions. All such changes and modifications are also included within the scope of the present invention. Accordingly, the scope of the invention should be defined by the appended claims and legal equivalent thereof.

The invention claimed is:

1. A method for the treatment of inflammatory bowel disease in a subject in need, comprising administration of a therapeutically effective amount of a medicament comprising koumine or a pharmaceutically acceptable salt thereof to the subject, wherein the koumine has a structure of Formula (I):

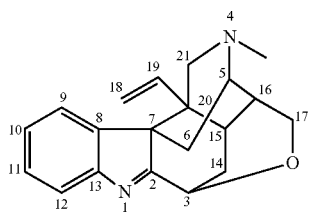

Formula (I)

wherein the inflammatory bowel disease is ulcerative colitis or Crohn's disease.

2. The method according to claim 1, wherein the medicament is adapted to be administered to ameliorate or eliminate a pathological change of the inflammatory bowel disease, alleviate or eliminate one or more symptoms of the inflammatory bowel disease, slow or stop progression of the inflammatory bowel disease, lessen the severity of the inflammatory bowel disease, reduce recurrence of the inflammatory bowel disease, and/or improve prognosis of the inflammatory bowel disease.

3. The method according to claim 1, wherein the medicament comprises the koumine or the pharmaceutically acceptable salt thereof as a sole active ingredient.

4. The method according to claim 1, wherein the medicament further comprises one or more other active ingredients.

5. The method according to claim 1, wherein the pharmaceutically acceptable salt comprises a salt formed from koumine and an organic or inorganic acid.

6. The method according to claim 5, wherein the pharmaceutically acceptable salt is selected from hydrochloride, sulphate, hydrobromide, hydroiodide, nitrate, bisulphate, phosphate, acid phosphate, citrate, acetate, oxalate, isonicotinate, lactate, salicylate, acid citrate, tartrate, oleate, tannate, pantothenate, bitartrate, ascorbate, succinate, maleate, gentisate, fumarate, gluconate, glucuronate, formate, benzoate, glutamate, mesylate, ethanesulfonate, benzenesulfonate, tosylate and pamoate.

7. The method according to claim 6, wherein the pharmaceutically acceptable salt is koumine hydrochloride.

8. The method according to claim 1, wherein the medicament comprises one or more pharmaceutically acceptable carriers.

9. The method according to claim 8, wherein the carriers are selected from excipients, disintegrants, diluents, binders, glidants, lubricants, pH adjusters, preservatives, dispersants, suspension aids, ointment bases, emulsifiers, emollients, penetration enhancers, surfactants, propellants, flavoring agents, sweeteners, drug release modifiers and any combination thereof.

10. The method according to claim 1, wherein the administration of the medicament is oral administration, parenteral administration, topical administration, transdermal administration, enema administration or rectal administration.

11. The method according to claim 1, wherein the medicament is in the form of a tablet, a capsule, granules, a syrup, a patch, an enema, a suppository, an emulsion or a gel.

12. The method according to claim 1, wherein the subject is a mammal.

13. The method according to claim 1, wherein the subject is a human.

14. The method according to claim 3, wherein the koumine or the pharmaceutically acceptable salt thereof is present in the medicament at an amount of 0.001 mg to 500 mg.

15. The method according to claim 3, wherein the koumine or the pharmaceutically acceptable salt thereof is present in the medicament at an amount of 0.1-20 mg.

16. The method according to claim 4, wherein the koumine or the pharmaceutically acceptable salt thereof and the one or more other active ingredients are present in the medicament at an amount of 0.001 mg to 500 mg.

17. The method according to claim 4, wherein the koumine or the pharmaceutically acceptable salt thereof and the one or more other active ingredients are present in the medicament at an amount of 0.1-20 mg.

* * * * *